(12) United States Patent
Matsuo (10) Patent No.: US 9,668,913 B2
(45) Date of Patent: Jun. 6, 2017

(54) BIODEGRADABLE DISPOSABLE HAND WARMER

(75) Inventor: Atsushi Matsuo, Osaka (JP)

(73) Assignee: Kobayashi Pharmaceutical Co., Ltd., Osaka-shi (JP)

( * ) Notice: Subject to any disclaimer, the term of this patent is extended or adjusted under 35 U.S.C. 154(b) by 0 days.

(21) Appl. No.: 13/634,451

(22) PCT Filed: Mar. 25, 2011

(86) PCT No.: PCT/JP2011/057380
§ 371 (c)(1),
(2), (4) Date: Sep. 12, 2012

(87) PCT Pub. No.: WO2011/125547
PCT Pub. Date: Oct. 13, 2011

(65) Prior Publication Data
US 2013/0008425 A1    Jan. 10, 2013

(30) Foreign Application Priority Data
Mar. 31, 2010    (JP) .................................. 2010-082456

(51) Int. Cl.
| | |
|---|---|
| *A41D 13/005* | (2006.01) |
| *F24J 1/00* | (2006.01) |
| *A61F 7/03* | (2006.01) |
| *A61F 7/00* | (2006.01) |

(52) U.S. Cl.
CPC ...... *A61F 7/034* (2013.01); *A61F 2007/0036* (2013.01)

(58) Field of Classification Search
CPC .......................... A61F 2007/0036; A61F 7/034

USPC .......................................................... 126/204
See application file for complete search history.

(56) References Cited

U.S. PATENT DOCUMENTS

| | | | |
|---|---|---|---|
| 3,840,512 A | 10/1974 | Brackman et al. | |
| 3,994,855 A | * 11/1976 | Boberg .......................... | 523/126 |
| 4,101,720 A | * 7/1978 | Taylor et al. ................. | 523/126 |
| 4,156,666 A | 5/1979 | Odate et al. | |
| 4,256,851 A | * 3/1981 | Taylor et al. ................. | 523/124 |
| 4,282,005 A | * 8/1981 | Sato et al. ............... | 126/263.02 |
| 4,360,606 A | 11/1982 | Tobias et al. | |
| 4,461,853 A | * 7/1984 | Gilead et al. ................. | 523/126 |

(Continued)

FOREIGN PATENT DOCUMENTS

| | | |
|---|---|---|
| CN | 1760310 A | 4/2006 |
| CN | 101338182 A | 1/2009 |

(Continued)

OTHER PUBLICATIONS

International Search Report dated Jun. 21, 2011, issued for PCT/JP2011/057380.

*Primary Examiner* — Steven B McAllister
*Assistant Examiner* — Steven Anderson, II
(74) *Attorney, Agent, or Firm* — Locke Lord LLP; James E. Armstrong, IV; Nicholas J. DiCeglie, Jr.

(57) ABSTRACT

An object of the present invention is to provide a disposable body warmer that exhibits sufficient physical properties (strength) of the inner bag during use, and that is excellent in biodegradability after use. The disposable body warmer is prepared by allowing an exothermic composition comprising potassium chloride and/or sodium chloride to be contained in an inner bag comprising an oxidative degradation agent.

11 Claims, 4 Drawing Sheets

(56) References Cited

U.S. PATENT DOCUMENTS

| | | | |
|---|---|---|---|
| 4,476,255 A * | 10/1984 | Bailey et al. | 523/125 |
| 4,517,318 A | 5/1985 | Miyoshi et al. | |
| 4,649,895 A | 3/1987 | Yasuki et al. | |
| 4,931,488 A | 6/1990 | Chiquet | |
| 4,938,645 A | 7/1990 | Wollar | |
| 4,983,645 A * | 1/1991 | Schwab | 522/47 |
| 5,096,939 A * | 3/1992 | Mor | 523/125 |
| 5,308,906 A * | 5/1994 | Taylor et al. | 524/398 |
| 5,565,503 A | 10/1996 | Garcia et al. | |
| 5,854,304 A * | 12/1998 | Garcia et al. | 523/124 |
| 5,975,074 A * | 11/1999 | Koiso et al. | 126/204 |
| 7,652,228 B2 * | 1/2010 | Igaki et al. | 219/401 |
| 2008/0064996 A1* | 3/2008 | Bretl et al. | 602/21 |
| 2008/0251062 A1* | 10/2008 | Dodo | 126/263.02 |
| 2009/0112231 A1* | 4/2009 | Luizzi | 606/134 |

FOREIGN PATENT DOCUMENTS

| | | |
|---|---|---|
| JP | 06-075436 U | 10/1994 |
| JP | 2002-301099 A | 10/2002 |
| JP | 2002-542313 A | 12/2002 |
| JP | 2003-250830 A | 9/2003 |
| JP | 2006-307113 A | 11/2006 |
| WO | WO-88/09354 A1 | 12/1988 |
| WO | WO-92/11298 A1 | 7/1992 |
| WO | WO-94/13735 A1 | 6/1994 |
| WO | WO-00/59996 A1 | 10/2000 |

\* cited by examiner

BIODEGRADABLE DISPOSABLE HAND WARMER

CROSS REFERENCE TO RELATED APPLICATIONS

This application is related to co-pending application: "DEGRADATION PROMOTER OF BIODEGRADABLE RESIN MOLDED BODY, AND USE THEREOF" filed even date herewith in the name of Atsushi Matsuo, as a national stage application of International Application No. PCT/JP2011/057381, filed Mar. 25, 2011, which application is assigned to the assignee of the instant application and which co-pending application is also incorporated by reference herein.

TECHNICAL FIELD

The present invention relates to a biodegradable disposable body warmer. More specifically, the present invention relates to a disposable body warmer that can maintain sufficient physical properties (strength) of the inner bag during use, and that is excellent in biodegradability after use.

BACKGROUND ART

A known general disposable body warmer comprises a breathable inner bag (enclosing bag) containing an exothermic composition, which generates heat in the presence of air; when in use, the inner bag is taken out from a non-breathable outer bag. Disposable body warmers are excellent in convenience as a heat-retaining material for the body, are provided inexpensively, and are thus recently consumed in large quantities. Disposable body warmers are subjected to disposal after use by means of landfilling or incineration. However, the inner bags used in known disposable body warmers are formed from petroleum-based plastic materials (hydrolysis-resistant materials), such as polyethylene, polypropylene, and polystyrene. Therefore, toxic gas is generated if the inner bags are disposed by incineration, and no biodegradation occurs in soil if disposed by landfilling, resulting in adverse effects on the environment.

In view of the above, attempts have recently been made to solve the above-described problems by allowing a disposable body warmer to exhibit biodegradability. Hitherto, as a technique to allow a disposable body warmer to exhibit biodegradability, there have been reports that state that a biodegradable plastic (i.e., hydrolytic biodegradable plastic), which is capable of being degraded to low molecular compound(s) through hydrolysis degradation and subsequent microbial degradation, is used in the inner bag. For example, Patent Literature 1 proposes a technique wherein a sheet material formed from a laminate consisting of a nonwoven fabric in which cellulose-based natural fibers are bonded to each other with chitosan and a film sheet mainly composed of a starch is used as the inner bag of a biodegradable disposable body warmer. Patent Literature 2 proposes a technique of using a laminate of a polylactic acid film and a natural fiber in the inner bag of a biodegradable disposable body warmer. Further, Patent Literature 3 proposes a biodegradable disposable body warmer including a biodegradable inner bag containing an exothermic composition comprising iron powder as a main component and a sodium free salt.

With respect to a disposable body warmer, the inner bag is subjected, while in use, to physical stress, such as crumpling and folding, as well as heat stress attributable to heat generation; the inner bag is thus thereby exposed to harsh environments. For this reason, the inner bag is required to exhibit physical properties (strength) that can withstand such harsh environments. However, an inner bag formed by using a hydrolytic biodegradable plastic has insufficient strength, and is gradually weakened while the disposable body warmer is in use. Therefore, known biodegradable disposable body warmers that have been reported suffer from problems such that the feeling of use worsens over time of use, and the exothermic composition is easily leaked.

As such, known disposable body warmers are not capable of exhibiting both biodegradability and desired physical properties (strength), and biodegradable disposable body warmers are thus not actually available on the market at present.

Meanwhile, an oxidative degradation agent, which allows plastic materials to depolymerize by oxidative degradation, has recently been developed (Patent Literature 4). When a plastic material comprising such a degradation agent is disposed by landfilling or other means, the plastic material is depolymerized by oxidative degradation, and then spontaneously degraded through microbial degradation. The aforementioned degradation agent is also applicable to petroleum-based plastic materials (hydrolysis-resistant materials) having high strength, and is thus attracting attention as an alternative technique for hydrolytic biodegradable plastics. However, regarding waste disposed by landfilling or other means, it is important to increase the degradation rate to thereby reduce the burden on the environment as much as possible; nevertheless, the techniques to improve the rate of degradation of a plastic material comprising such a degradation agent have not yet been sufficiently studied.

CITATION LIST

Patent Literature

Patent Literature 1: Japanese Unexamined Utility Model Patent Publication No. H6-75436
Patent Literature 2: Japanese Unexamined Patent Publication No. 2003-250830
Patent Literature 3: Japanese Unexamined Patent Publication No. 2002-301099
Patent Literature 4: Japanese Unexamined Patent Publication No. 2002-542313

SUMMARY OF INVENTION

Technical Problem

The present invention aims to provide a disposable body warmer that exhibits sufficient physical properties (strength) of the inner bag during use, and that is excellent in biodegradability after use.

Solution to Problem

The present inventor carried out intensive research to solve the aforementioned problems, and found the following. Specifically, a disposable body warmer comprising an inner bag and an exothermic composition, the exothermic composition being contained in the inner bag, the inner bag comprising an oxidative degradation agent, and the exothermic composition comprising potassium chloride and/or sodium chloride, can maintain sufficient physical properties (strength) during use and can achieve improved biodegradability after use. The inventor conducted further research based on such findings, and accomplished the present invention.

More specifically, the present invention provides the following disposable body warmer.

Item 1. A biodegradable disposable body warmer comprising an inner bag and an exothermic composition, the exothermic composition being contained in the inner bag, the inner bag comprising an oxidative degradation agent, and the exothermic composition comprising at least one member selected from the group consisting of potassium chloride and sodium chloride.

Item 2. The biodegradable disposable body warmer according to Item 1, wherein the inner bag is formed from a laminate comprising a breathable resin film laminated on a woven or nonwoven fabric.

Item 3. The biodegradable disposable body warmer according to Item 2, wherein the resin forming the breathable resin film is polyolefin.

Item 4. The biodegradable disposable body warmer according to Item 2 or 3, wherein the fiber material forming the woven or nonwoven fabric is a synthetic fiber.

Item 5. The biodegradable disposable body warmer according to any one of Items 1 to 4, wherein the exothermic composition comprises potassium chloride, an iron powder, a water-retaining agent, and water.

Item 6. The biodegradable disposable body warmer according to any one of Items 1 to 5, wherein the oxidative degradation agent is at least one member selected from the group consisting of carboxylic acid metal salts, hydroxy carboxylic acids, transition metal compounds, rare earth compounds, and aromatic ketones.

Item 7. The biodegradable disposable body warmer according to any one of Items 1 to 6, wherein the oxidative degradation agent is a combination of a carboxylic acid salt and a rare earth compound.

Advantageous Effects of Invention

In the biodegradable disposable body warmer of the present invention, potassium chloride and/or sodium chloride included in the exothermic composition can specifically promote inner bag degradation induced by an oxidative degradation agent. Therefore, even if the inner bag of the present invention is, for example, disposed in landfills or in fields or mountains after use, it is quickly degraded, causing no environmental contamination.

Further, the biodegradable disposable body warmer of the present invention causes no physical property (strength) deterioration, which results in problems in use, such that when the body warmer generates heat, the inner bag is weakened or the exothermic composition leaks out of the inner bag. The biodegradable disposable body warmer of the present invention thus has sufficient practical value, as well.

BRIEF DESCRIPTION OF DRAWINGS

The reference number 1 is a biodegradable disposable body warmer, 2 is an exothermic composition, 3 is an inner bag, 3a is a woven or nonwoven fabric, and 3b is a breathable resin film.

DESCRIPTION OF EMBODIMENTS

One of the features of the biodegradable disposable body warmer of the present invention is that an exothermic composition comprising potassium chloride and/or sodium chloride is contained in an inner bag comprising an oxidative degradation agent. The biodegradable disposable body warmer of the present invention is described below in detail.

Exothermic Composition

In the present invention, an exothermic composition comprising potassium chloride and/or sodium chloride is used as a heat source of the disposable body warmer. Potassium chloride and sodium chloride in the exothermic composition function to specifically facilitate inner bag degradation induced by an oxidative degradation agent mentioned below, and to improve biodegradation properties of the biodegradable disposable body warmer of the present invention after use. Potassium chloride and sodium chloride further function to activate the surface of the iron powder included in the exothermic composition to accelerate the oxidation reaction of the iron. Potassium chloride, in particular, has a remarkably high function to specifically promote inner bag degradation induced by an oxidative degradation agent, and is thus preferably used in the present invention.

In the present invention, either potassium chloride or sodium chloride may be used individually, or they may be used in combination.

In the present invention, the proportion of potassium chloride and/or sodium chloride in the exothermic composition is not particularly limited; for example, they are used in an amount of about 0.5 to 10 mass %, preferably about 0.5 to 5 mass %, and more preferably about 0.5 to 3 mass %, based on the total mass of the exothermic composition.

In order to further improve the biodegradability of the disposable body warmer of the present invention, potassium chloride and/or sodium chloride are preferably contained in the exothermic composition in an amount of, for example, about 4 to 2,800 parts by mass, preferably about 10 to 2,600 parts by mass, and more preferably about 50 to 2,400 parts by mass, per 100 parts by mass of the oxidative degradation agent incorporated in the inner bag.

In the present invention, an exothermic composition generates heat upon contact with air and comprises components required for the heat generation, in addition to potassium chloride. The components required for the heat generation are not particularly limited. A preferable example of the exothermic composition used in the present invention is a composition comprising at least one member selected from the group consisting of potassium chloride and sodium chloride; and an iron powder, a water-retaining agent, and water.

In the exothermic composition, the total mass of potassium chloride and/or sodium chloride, an iron powder, a water-retaining agent, and water is preferably about 80 to 100 mass %.

Iron powder generates heat through a reaction with oxygen in air. Examples of iron powder used in the exothermic composition include reduced iron, cast iron, and the like. These can be used singly, or in a combination of two or more.

The shape of the iron powder is not particularly limited; it may be in any shape, such as a granular or fibrous shape.

The particle diameter of granular iron powder is not particularly limited. The diameter thereof is usually within the range of about 10 to 300 µm, and preferably about 10 to 100 µm. The particle diameter of iron powder can be calculated by introducing 100 g of a sample to be measured (iron powder, etc.) into an electric vibratory screen provided with sieves of, sequentially from the top, 700 µm, 650 µm, 500 µm, 400 µm, 300 µm, 250 µm, 100 µm, 50 µm, and 10 µm; vibrating the sieves for 15 minutes; and measuring the amount remaining on each sieve, as well as the amount passed through each sieve. For example, when iron powder having a particle diameter of 10 to 300 µm is used, iron powder that completely passes through the 300 µm sieve and that remains on any one or all of the 10 to 250 µm sieves can be used.

The proportion of iron powder in the exothermic composition is not particularly limited. For example, the proportion thereof is about 30 to 80 mass %, and preferably about 45 to 65 mass %, based on the total mass of the exothermic composition.

A water-retaining agent is a substance that functions to retain water. Examples of a water-retaining agent used in the exothermic composition include, but are not particularly limited to, porous substances, water-absorbent resins, and the like.

Specific examples of porous substances used as a water-retaining agent include activated carbon, wood flour, perlite, expanded vermiculite, vermiculite, and the like.

Activated carbon can trap air in the fine pores on the surface and promote oxygen supply, and can also cause heat retention so as not to cause variations in the heat radiation temperature. Activated carbon has a very porous internal structure, and can thus give particularly excellent water-retention ability. Further, activated carbon not only absorbs water well, but also absorbs water vapor evaporated by the heat generated from the exothermic composition, and helps the prevention of the escape of the water vapor. Therefore, activated carbon is also useful as a water-retaining substance. Activated carbon can also absorb odor generated by oxidation of iron powder. A preferable example of the activated carbon includes an activated carbon prepared from a coconut shell, wood, charcoal, coal, bone coal, or the like. Examples of the shapes of the activated carbon include a granular shape, a fibrous shape, and the like. Activated carbons having such shapes can be used singly, or in a combination of two or more. In the present invention, in particular, a granular activated carbon is preferably used. When a granular activated carbon is used, the particle diameter is preferably about 10 to 300 µm, and more preferably about 10 to 100 µm. This particle diameter is measured in accordance with the aforementioned method for measuring the particle diameter of iron powder.

Among the porous substances, activated carbon, vermiculite, and expanded vermiculite are preferable, with activated carbon and vermiculite being more preferable, and activated carbon being still more preferable. These porous substances can be used singly, or in a combination of two or more.

Specific examples of water-absorbent resins used as a water-retaining agent include isobutylene-maleic anhydride copolymers, polyvinyl alcohol-acrylic acid copolymers, starch-acrylic acid salt graft copolymers, crosslinked polyacrylates, acrylic acid salt-acrylic ester copolymers, acrylic acid salt-acrylamide copolymers, crosslinked polyacrylonitrile acid salts, and the like. Of these water-absorbent resins, crosslinked polyacrylates are preferable. These water-absorbent resins can be used singly, or in a combination of two or more. The particle diameter of water-absorbent resin is usually about 100 to 500 µm, and preferably about 250 to 400 µm. This particle diameter is measured in accordance with the aforementioned method for measuring the particle diameter of iron powder.

In the above exothermic composition, either one of a porous substance or water-absorbent resin may be used as the water-retaining agent, or they may be used in combination. The water-retaining agent used in the exothermic composition is preferably, for example, a porous substance, or a combination of a porous substance and a water-absorbent resin; more preferably activated carbon, or a combination of activated carbon, other porous substances (porous substances other than activated carbon), and a water-absorbent resin; and still more preferably a combination of activated carbon, vermiculite, and a crosslinked polyacrylate.

The proportion of the water-retaining agent in the exothermic composition is not particularly limited. For example, the water-retaining agent is used in an amount of about 2 to 30 mass %, preferably about 5 to 20 mass %, based on the total mass of the exothermic composition. More specifically, in a case where a porous substance is used singly as the water-retaining agent, it is used in an amount of about 10 to 30 mass %, preferably about 10 to 20 mass %, based on the total mass of the exothermic composition. In a case where a water-absorbent resin is used singly as the water-retaining agent, it is used in an amount of about 2 to 10 mass %, preferably about 2 to 7 mass %, based on the total mass of the exothermic composition. Further, in a case where a porous substance and a water-absorbent resin are used in combination as the water-retaining agent, a porous substance is used in an amount of 5 to 20 mass % and a water-absorbent resin is used in an amount of 1 to 10 mass %, based on the total mass of the exothermic composition; and preferably a porous substance is used in an amount of 7 to 20 mass % and a water-absorbent resin is used in an amount of 1 to 5 mass %, based on the total mass of the exothermic composition. In particular, in a case where a combination of activated carbon, other porous substances, and a water-absorbent resin is used as the water-retaining agent, activated carbon is used in an amount of 3 to 20 mass %, other porous substances are used in an amount of 1 to 10 mass %, and a water-absorbent resin is used in an amount of 1 to 10 mass %, based on the total mass of the exothermic composition; and preferably activated carbon is used in an amount of 5 to 15 mass %, other porous substances are used in an amount of 1 to 5 mass %, and a water-absorbent resin is used in an amount of 1 to 5 mass %, based on the total mass of the exothermic composition.

As water incorporated in the exothermic composition, for example, distilled water or tap water can be used. The proportion of water in the exothermic composition is not particularly limited; for example, it is used in an amount of 1 to 40 mass %, preferably 20 to 30 mass %, based on the total mass of the exothermic composition.

In addition to the components mentioned above, the exothermic composition may contain other additives that can be incorporated in an exothermic composition, as required. Examples of such additives include metal salts other than potassium chloride and sodium chloride. Specific examples of metal salts other than potassium chloride and sodium chloride include ferric sulfate, potassium sulfate, sodium sulfate, manganese sulfate, magnesium sulfate, and like sulfates; cupric chloride, calcium chloride, manganese chloride, magnesium chloride, cuprous chloride, and like chlorides; and the like.

The exothermic composition is prepared by mixing each component. The preparation of the exothermic composition may be performed under vacuum or in an inert gas atmosphere, as required, to suppress heat generation during the preparation. The exothermic composition may be prepared by performing mixing in accordance with a method disclosed in U.S. Pat. No. 4,649,895.

Inner Bag

In the present invention, an inner bag comprising an oxidative degradation agent is used to contain the above-described exothermic composition.

The inner bag is not particularly limited, as long as it has breathability and can contain an exothermic composition. To inhibit leakage of the contained exothermic composition, and to also provide excellent feeling of use of the disposable body warmer, the inner bag is preferably formed from a laminate comprising a breathable resin film laminated on a woven or nonwoven fabric. Here, when such a laminate is used to form the inner bag, the breathable resin film is provided inside (the side that contacts with an exothermic composition) of the body warmer, and the woven or nonwoven fabric is provided outside (the side that is exposed to the external world) of the body warmer.

The resin that forms the breathable resin film used in the laminate is not particularly limited; a thermoplastic synthetic resin is preferably used. Specific examples of thermoplastic synthetic resins that constitute the breathable resin film include polyolefin (e.g., polyethylene and polypropylene), polystyrene, polyvinyl chloride, polyvinylidene chloride, polyamide, polyester, polyvinyl alcohol, polyurethane, ethylene-vinylacetate copolymers, polycarbonates, and the like. Of these thermoplastic resins, in order to maintain strength during use and to allow the inner bag to exhibit excellent biodegradability after use, resins exhibiting hydrolysis resistance, such as polyolefin (e.g., polyethylene and polypropylene), polystyrene, polyvinyl chloride, polyvinylidene chloride, and polyamide are preferable, with polyolefins being more preferable, polyethylene and polypropylene being still more preferable, and polyethylene being even more preferable. These thermoplastic synthetic resins may be used singly, or in a combination of two or more.

In the breathable resin film, fine pores are provided so as to allow air to pass therethrough, thereby ensuring the breathability. Such pores are desirably fine to such an extent that the contained exothermic composition does not pass them through. Methods for providing fine pores with a resin film are known. Examples of such a method include a method comprising bringing a resin film into contact with a rotating roll comprising a row of disc-shaped members, each disc-shaped member having blades on the circumference, to form fine pores; a method comprising stretching a resin sheet containing an inorganic filler such as calcium carbonate to form fine pores in the stretched resin film; and the like.

Examples of fiber materials forming the woven or nonwoven fabric, on which the breathable resin film is laminated, include nylon, vinylon, polyester, rayon, acetate, acrylic, polyolefin (e.g., polyethylene and polypropylene), polyvinyl chloride, and like synthetic fibers; cotton, hemp, silk, and like natural fibers; and the like. Of these fiber materials, from the viewpoint of providing both excellent feeling of use and excellent biodegradability after use, polyolefins are preferable, with polyethylene and polypropylene being more preferable, and polypropylene being still more preferable. The woven or nonwoven fabric preferably has a basis weight of about 20 to 100 $g/m^2$.

A lamination method can usually be conducted to obtain a laminate of a breathable resin film and a woven or nonwoven fabric. A well-known arbitrary method can be applied to the lamination method. Examples thereof include a lamination method by means of thermal bonding, and a lamination method with the use of an adhesive, such as hot melt adhesive, acrylic adhesive, or urethane adhesive. In the laminate used as the inner bag, the breathable resin film and woven or nonwoven fabric may be thoroughly bonded to each other; or, alternatively, may be partially bonded so as to ensure flexibility.

The inner bag used in the present invention comprises an oxidative degradation agent (sometimes referred to as a "chemical degradation agent"). Because an oxidative degradation agent is incorporated, even if the inner bag is formed from materials that cannot be naturally degraded, such materials can be oxidatively degraded after use and depolymerized, and can then be subjected to microbial degradation. Further, in the disposable body warmer of the present invention, the coexistence of an oxidative degradation agent in the inner bag and potassium chloride in the exothermic composition remarkably improves the rate of the degradation of the inner bag after it is used.

In the present invention, as long as an oxidative degradation agent is incorporated in the inner bag, the incorporation mode is not particularly limited. For example, when the inner bag is formed from a laminate of a breathable resin film and a woven or nonwoven fabric, an oxidative degradation agent may be incorporated in at least either one of the breathable resin film, or woven or nonwoven fabric. However, from the viewpoint of further enhancing the biodegradability after use, an oxidative degradation agent is desirably incorporated in both the breathable resin film and the woven or nonwoven fabric.

In the present invention, an oxidative degradation agent refers to a substance that oxidatively degrades a polymer that forms the inner bag to allow the polymer to be degraded to low molecular compound(s) to such an extent that microbial degradation can be carried out.

An oxidative degradation agent is known in this technical field (for example, U.S. Pat. Nos. 3,840,512, 3,994,855, 4,101,720, 4,156,666, 4,256,851, 4,360,60, 4,461,853, 4,476,255, 4,517,318, 4,931,488, 4,983,645, 5,096,939, 5,308,906, 5,565,503, and 5,854,304; and WO88/09354, WO92/11298, WO94/13735, WO00/59996, and the like). Preferable examples of oxidative degradation agents include carboxylic acid metal salts, hydroxycarboxylic acids, transition metal compounds (U.S. Pat. No. 5,308,906), rare earth compounds, aromatic ketones, and the like. Other usable oxidative degradation agents include combinations of carboxylic acid metal salts and hydroxy carboxylic acids (U.S. Pat. No. 5,854,304), combinations of carboxylic acid metal salts and fillers (U.S. Pat. No. 5,565,503), and the like. In the present invention, these oxidative degradation agents can be used singly, or in a combination of two or more.

As carboxylic acid metal salts used as an oxidative degradation agent, metal salts of aliphatic carboxylic acids having 10 to 20 carbon atoms are preferable, and metal stearate is more preferable. Examples of a metal atom constituting the carboxylic acid metal salt include cobalt, cerium, iron, aluminium, antimony, barium, bismuth, cadmium, chromium, copper, gallium, lanthanum, lead, lithium, magnesium, mercury, molybdenum, nickel, calcium, rare earth, silver, sodium, strontium, tin, tungsten, vanadium, yttrium, zinc, zirconium, and the like. As a carboxylic acid metal salt used as an oxidative degradation agent, stearates of metals such as cobalt, cerium, and iron are preferable.

Examples of hydroxy carboxylic acids used as an oxidative degradation agent include monohydroxy tricarboxylic acids such as citric acid; polyhydroxy dicarboxylic acids such as trihydroxy glutaric acid and saccharic acid; dihydroxy dicarboxylic acids such as tartaric acid; monohydroxy dicarboxylic acids such as tartronic acid and malic acid; polyhydroxy monocarboxylic acids such as erythric acid, arabic acid, and mannitic acid; dihydroxy monocarboxylic acids such as glyoxylic acid and glyceric acid; and the like. These hydroxyl carboxylic acids can be used singly, or in a combination of two or more.

Examples of fillers used as one component of an oxidative degradation agent include inorganic carbonate, synthetic carbonate, nepheline syenite, talc, magnesium hydroxide, aluminium hydroxide, diatomaceous earth, natural or synthetic silica, calcined clay, and the like. It is desirable that these fillers have a particle diameter of less than 150 meshes. The fillers can be used singly, or in a combination of two or more.

Examples of transition metal compounds used as an oxidative degradation agent include salts of cobalt or magnesium, preferably aliphatic carboxylic acid ($C_{12}$ to $C_{20}$) salts of cobalt or magnesium, and more preferably cobalt stearate, cobalt oleate, magnesium stearate, and magnesium oleate. These transition metal compounds can be used singly, or in a combination of two or more.

Examples of rare earth compounds used as an oxidative degradation agent include rare earths belonging to periodic table Group 3A, and oxides thereof. Specific examples thereof include cerium (Ce), yttrium (Y), neodymium (Nd), rare earth oxides, hydroxides, rare earth sulfates, rare earth nitrates, rare earth acetates, rare earth chlorides, rare earth carboxylates, and the like. More specific examples thereof include cerium oxide, ceric sulfate, ceric ammonium sulfate, ceric ammonium nitrate, cerium acetate, lanthanum nitrate, cerium chloride, cerium nitrate, cerium hydroxide, cerium octylate, lanthanum oxide, yttrium oxide, scandium oxide, and the like. These rare earth compounds may be used singly, or in a combination of two or more.

Examples of aromatic ketones used as an oxidative degradation agent include benzophenone, anthraquinone, anthrone, acetylbenzophenone, 4-octylbenzophenone, and the like. These aromatic ketones may be used singly, or in a combination of two or more.

In the biodegradable disposable body warmer of the present invention, from the viewpoint of further facilitating biodegradability after use, a combination of a carboxylic acid salt and a rare earth compound is preferably used as an oxidative degradation agent. A preferable example of an oxidative degradation agent used in the present invention is a product commercially available under the trade name "P-Life" (produced by P-Life Japan Inc.).

An oxidative degradation agent generally oxidatively degrades, under the action of light, heat, air, etc., a polymer that forms a resin molded body to allow the polymer to be degraded to low molecular compound(s) to such an extent that microbial degradation can be carried out. In the present invention, among oxidative degradation agents, an oxidative degradation agent that exerts its effects on oxidative degradation of a polymer upon exposure to light (ultraviolet light) (hereinafter referred to as a "light-requiring oxidative degradation agent") is preferably used. An inner bag comprising a light-requiring oxidative degradation agent is not degraded under shaded conditions. Therefore, by keeping the inner bag in a shaded atmosphere (e.g., in a shaded space, a light-resistant container, or a light-proof bag) in the pre-use stage, i.e., during production, distribution, and storage, the inner bag can maintain desired functions without causing durability deterioration until use. Examples of such light-requiring oxidative degradation agents include an oxidative degradation agent containing a rare earth compound. More specifically, "P-life" (tradename, produced by P-Life Japan Inc.) is exemplified.

In the present invention, the proportion of oxidative degradation agent in the inner bag is suitably determined depending on, for example, the type of the oxidative degradation agent and the type of the constituent materials of the inner bag. For example, an oxidative degradation agent may be used in an amount of 0.48 to 3.8 mass %, preferably 0.72 to 3.1 mass %, and still more preferably 0.96 to 2.4 mass %, based on the total weight of the inner bag.

More specifically, in a case where a laminate comprising a breathable resin film laminated on a woven or nonwoven fabric is used to form the inner bag, for example, an oxidative degradation agent is used in an amount of 0.4 to 3 mass %, preferably 0.6 to 2.5 mass %, and more preferably 0.8 to 2 mass %, based on the total weight of the breathable resin film; and an oxidative degradation agent is used in an amount of 0.08 to 0.8 mass %, preferably 0.12 to 0.6 mass %, and more preferably 0.16 to 0.4 mass %, based on the total weight of the woven or nonwoven fabric.

An inner bag comprising an oxidative degradation agent can be produced by a known method. For example, a production method including the following procedures is exemplified: (1) a predetermined amount of oxidative degradation agent is added to a molten polymer for forming an inner bag, and the molten mixture is formed into pellets; (2) subsequently, the pellets are melted and formed into a shape of the material (e.g., fibrous or film-like shape) that forms an inner bag; and (3) the material obtained above, which is formed into a fibrous or film-like shape, is processed into a shape of the inner bag.

Biodegradable Disposable Body Warmer

The biodegradable disposable body warmer of the present invention is prepared by adhering the ends of the inner bag containing the exothermic composition to each other to form a seal.

The thus-prepared disposable body warmer is provided such that it is packaged in an airtight outer bag (preferably a light-blocking bag) that does not allow air to pass through; and, when it is used, the inner bag is taken out from the outer bag to be used as a body warmer.

In the biodegradable disposable body warmer of the present invention, the method for disposing the disposable body warmer is not limited; since it has a noteworthy property, i.e., excellent biodegradability, the body warmer of the present invention is preferably disposed by landfilling. When the biodegradable disposable body warmer of the invention is disposed in landfills or in fields or mountains after it is used, the inner bag is oxidatively degraded, and then undergoes microbial degradation. The duration for which the biodegradable disposable body warmer of the invention is eventually degraded varies depending on the disposal environment; it is usually degraded in about 0.5 to 3 years, to such an extent that the inner bag cannot be visually recognized.

EXAMPLES

The present invention is described below with reference to Examples. However, the scope of the invention is not limited to these Examples. The oxidative degradation agent-containing composition (with an oxidative degradation agent content of 80 to 90%) used in the Examples and Comparative Examples is a product commercially available under the trade name "P-Life" (a product of P-Life japan, Inc.; containing 50 to 70 wt % of an aliphatic monocarboxylic acid salt, 1.0 to 20 wt % of a rare earth compound, and 10 to 20% of a lubricant).

Example 1

Preparation of Disposable Body Warmer

1. Preparation of Exothermic Composition 55 mass % of iron powder having an average particle diameter of 50 μm, 13 mass % of activated carbon having an average particle diameter of 200 μm, 1 mass % of potassium chloride, 26 mass % of water, 3 mass % of vermiculite having a particle diameter of 100 μm, and 2 mass % of a crosslinked partial sodium salt of an acrylic acid polymer having a particle diameter of 380 μm were mixed to prepare an exothermic composition.

2. Preparation of Inner Bag Material

A resin sheet consisting of 98 mass % of polyethylene and 2 mass % of an oxidative degradation agent-containing material was brought into contact with a rotating roll comprising a row of disc-shaped members, each disc-shaped member having blades on the circumference, to prepare a breathable resin film (thickness: 40 μm) having fine pores with a size to achieve a value of about 13.5 to about 14.5 sec/100 cc when measured according to JIS P8117-1998 "Paper and Paperboard—Air Permeability Testing—the Gurley Method." Separately, a nonwoven fabric (basis weight: 25 g/m$^2$) was produced by spunbonding using a synthetic fiber consisting of 99.75 mass % of polypropylene and 0.25 mass % of an oxidative degradation agent-containing material.

The nonwoven fabric was laminated to the breathable resin film to prepare 1 g of a laminate 9.5 cm long and 120 cm wide (an inner bag; a laminate consisting of 0.7 g of the breathable, biodegradable resin film and 0.3 g of the biodegradable nonwoven fabric).

3. Preparation of Disposable Body Warmer

The exothermic composition prepared above was enclosed in the above-obtained laminate by three-side sealing. More specifically, the laminate obtained above was folded in two, and the portions about 7 mm from the outside were bonded together by thermocompression bonding at 130° C. Similarly, at one of the upper and lower opening ends, the portions about 7 mm from the outside were bonded together by thermocompression bonding at 130° C. Subsequently, after 20 g of the exothermic composition prepared above was inserted from the unbonded side of the inner bag, the portions about 7 mm from the outside of the unbound side were bonded together by thermocompression bonding at 130° C. to prepare a disposable body warmer. Next, the disposable body warmer thus prepared was placed into an (air-impermeable, light-blocking) outer bag comprising a polyvinylidene chloride coated film, and the outer bag was sealed. In the following Test Examples, at the beginning of the test, the disposable body warmer was removed from the outer bag, and used.

Example 2

Preparation of Disposable Body Warmer

A disposable body warmer was produced under the same conditions as in Example 1, except that 1 mass % of sodium chloride was used in place of 1 mass % of potassium chloride.

Test Example 1

Evaluation of Degradability and Exothermicity of the Disposable Body Warmers

The disposable body warmers obtained in Examples 1 and 2 were removed from the outer bags, and allowed to stand at room temperature for 24 hours until the end of the exothermic reaction. Thereafter, the disposable body warmers in which the exothermic reaction was finished were placed in a 50° C. thermostatic chamber, and stored for 12 days.

Immediately after the end of the exothermic reaction; and after 3 days; after 6 days; and after 12 days of storage at 50° C., each disposable body warmer was disassembled to remove the exothermic composition therefrom. An unpunctured portion of the inner bag was cut to a size of 2 cm×7 cm, and tensioned in the MD using a tensile testing machine (AGS-H, a product of Shimadzu Corporation) to determine the tensile strength. As a control, an inner bag not containing the exothermic composition was used. After the control inner bag was stored under the same conditions as above, the tensile strength was measured. Subsequently, the degradation promotion rate of each of the inner bags used in Examples 1 and 2 was measured according to the mathematical formula shown below. The higher the inner bag degradation rate, the lower the tensile strength. Accordingly, tensile strength is an indicator generally used in this technical field to evaluate the degree of degradation of inner bags.

Degradation promotion (%)={(Tensile strength of the control−Tensile strength of the inner bag obtained in the Example)/Tensile strength of the control}×100     [Math. Formula 1]

Further, the temporal changes in the exothermic temperature of the disposable body warmers obtained in Examples 1 and 2 were measured by the "disposable body warmer" temperature-measurement method of JIS S 4100. More specifically, first, a thermal device comprising a warmer and a water circulating thermostatic bath was used, and an underlayment and a covering were disposed on a thermal portion of the device; the surface temperature of the thermal portion was raised to 30° C. and maintained within the range of 30° C.±1° C. Subsequently, the disposable body warmers contained in the outer bags were held in an atmosphere at a temperature of 20±1° C. and a relative humidity of 55 to 70% in a constant-temperature, constant-humidity room for 2 hours or more. Thereafter, each disposable body warmer was removed from the outer bag to initiate the exothermic reaction. The exothermic composition within the inner bag was moved as far toward one side of the inner bag as possible; and the underlayment, a thermometry unit, the disposable body warmer, and the covering were stacked in this order and allowed to stand in the above-mentioned atmosphere in the constant-temperature, constant-humidity room to measure the changes in the exothermic temperature of each disposable body warmer over time.

Figure 1:
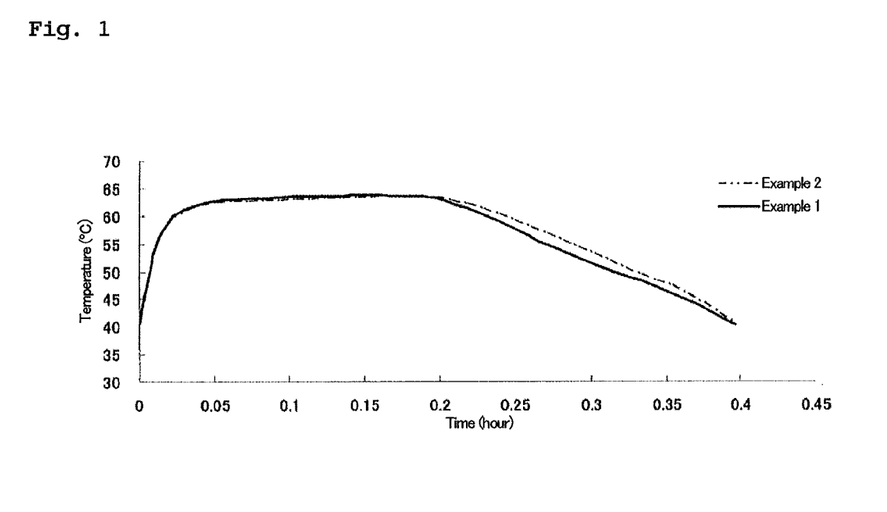
FIG. 1 shows the results of measuring the temporal changes in the exothermic temperature of the disposable body warmers (Examples 1 and 2) in Test Example 1.
Figure 2:
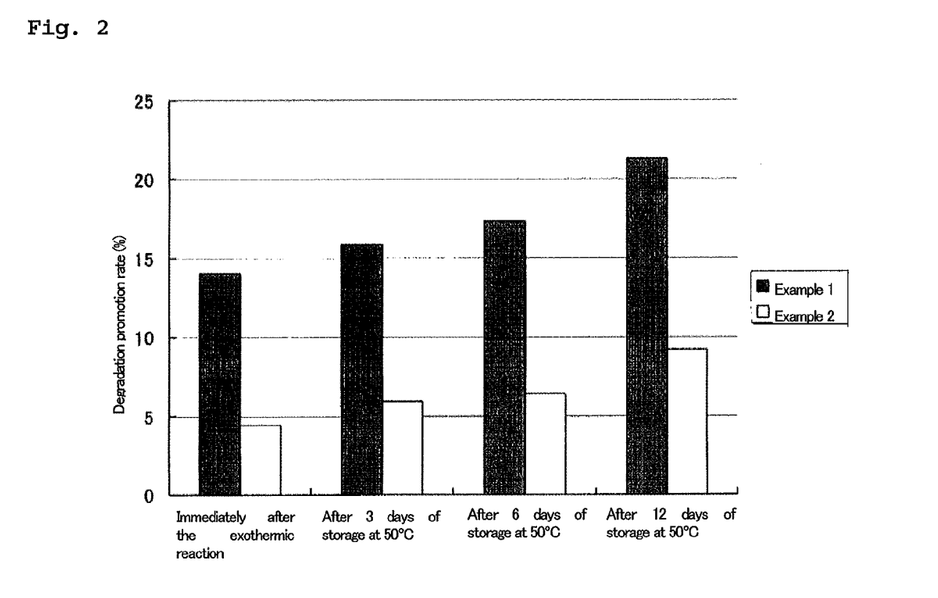
FIG. 2 shows the results of measuring the inner bag degradation promotion rate of the disposable body warmers (Examples 1 and 2) in Test Example 1.

FIG. 1 shows the results of measuring the temporal change in the exothermic temperature of the disposable body warmers obtained in Examples 1 and 2. FIG. 2 shows the results of measuring the inner bag degradation promotion rate of the disposable body warmers obtained in Examples 1 and 2.

As is clear from FIG. 1, there is no difference in exothermic properties between the disposable body warmers obtained in Examples 1 and 2. Further, the inner bags of the disposable body warmers obtained in Examples 1 and 2 exhibited highly promoted degradation rates, compared to the inner bag assessed as the control. Additionally, it was confirmed that compared to the case where sodium chloride was contained (Example 2), the disposable body warmer containing an exothermic composition comprising potassium chloride (Example 1) exhibited a remarkably high inner bag degradation promotion rate, and thus had excellent biodegradability. The inner bags of the disposable body warmers obtained in Examples 1 and 2 were such that even after the end of the exothermic reaction, strength reduction that would result in problems during use, such as brittleness and leakage of the exothermic composition, was not observed, and the physical properties required of body warmers were maintained.

Reference Test Example 1

Evaluation (No. 1) of Degradability of Non-Exothermic Composition-Containing Products 28.9 mass % of activated carbon having an average particle diameter of 200 μm, 2.2 mass % of potassium chloride, 57.8 mass % of water, 6.7 mass % of vermiculite having a particle diameter of 100 μm, and 4.4 mass % of a crosslinked partial sodium salt of an acrylic acid polymer having a particle diameter of 380 μm were mixed to prepare a non-exothermic composition. Twenty grams of the obtained non-exothermic composition was enclosed in the same inner bag as that used in Example 1 to prepare a non-exothermic composition-containing product (Reference Example 1).

Another non-exothermic composition-containing product (Reference Example 2) was prepared under the same conditions as in Reference Example 1, except that 2.2 mass % of sodium chloride was used in place of 2.2 mass % of potassium chloride.

These non-exothermic composition-containing products were stored in a 50° C. thermostatic chamber for 3 days. After 1 day of storage and after 3 days of storage, the inner bag degradation promotion rate was measured in the same manner as in Test Example 1 above.

Figure 3:
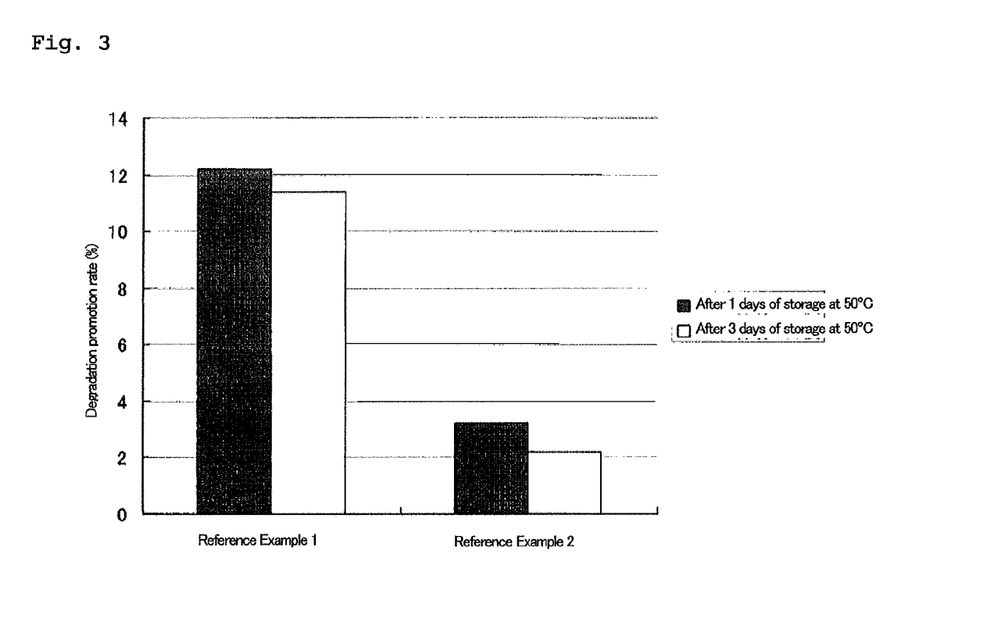
FIG. 3 shows the results of measuring the inner bag degradation promotion rate of the non-exothermic composition-containing products (Reference Examples 1 and 2) in Reference Test Example 1.

FIG. 3 shows the obtained results. The results show that, as in Test Example 1 above, the potassium chloride- or sodium chloride-containing products (Reference Examples 1 and 2) exhibited remarkably promoted inner bag degradation rates. In particular, the potassium chloride-containing product (Reference Example 1) exhibited a remarkably high inner bag degradation promotion rate, compared to the case where sodium chloride was contained (Reference Example 2). Considering the fact that the non-exothermic composition-containing products subjected to this test do not contain iron powder and thus do not produce heat even when in contact with air, it was confirmed that the degradation promotion of the inner bag comprising an oxidative degradation agent by the presence of potassium chloride or sodium chloride with the oxidative degradation agent is not greatly influenced by the temperature.

Reference Test Example 2

Evaluation (No. 2) of Degradability of Non-Exothermic Composition-Containing Products Non-exothermic composition-containing products were prepared under the same conditions as in Reference Example 1, except that 2.2 mass % of potassium dihydrogen phosphate (Reference Example 3), 2.2 mass % of magnesium sulfate (Reference Example 4), 2.2 mass % of manganese sulfate (Reference Example 5), 2.2 mass % of potassium sulfate (Reference Example 6), or 2.2 mass % of sodium sulfate (Reference Example 7) was used in place of 2.2 mass % of potassium chloride.

After the non-exothermic composition-containing products obtained in Reference Examples 3 to 7 were stored in a 50° C. thermostatic chamber for 1 day, the degradation promotion rate of each inner bag was measured in the same manner as in Test Example 1 above.

Figure 4:
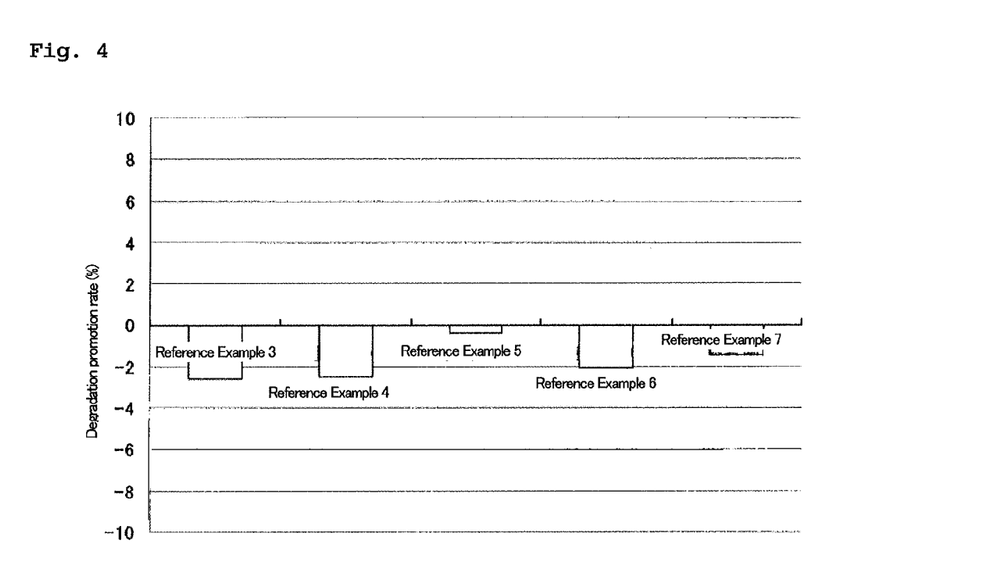
FIG. 4 shows the results of measuring the inner bag degradation promotion rate of the non-exothermic composition-containing products (References Examples 3 to 7) in Comparative Test Example 1.
Figure 5:
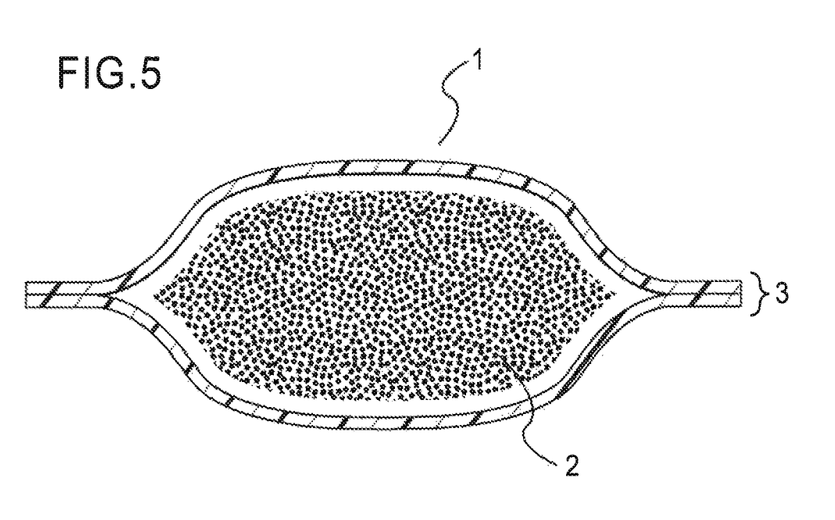
FIG. 5 shows an example of a structure of the claimed biodegradable disposable body warmer.
Figure 6:
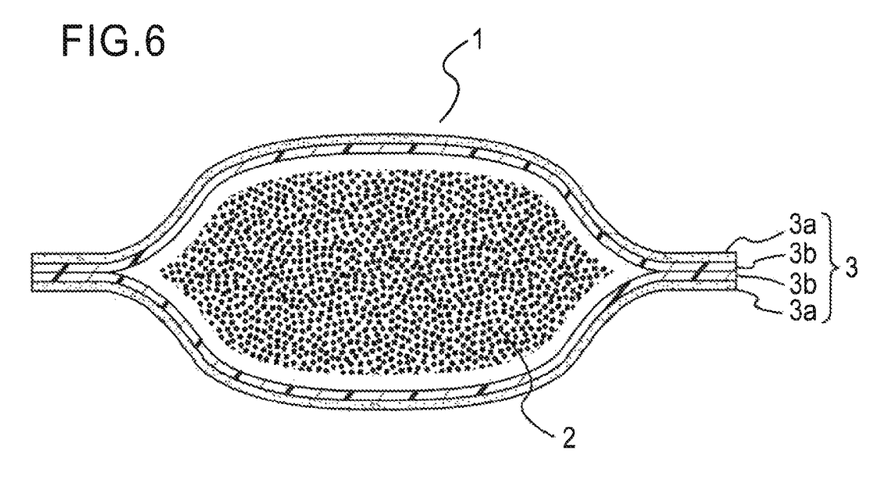
FIG. 6 shows another example of a structure of the claimed biodegradable disposable body warmer.

FIG. 4 shows the results. The results indicate that the inner bag degradation was not promoted at all in the products containing potassium dihydrogen phosphate, magnesium sulfate, manganese sulfate, potassium sulfate, or sodium sulfate (Reference Examples 3 to 7). These results clearly indicate that the inner bag degradation promotion effect observed in Examples 1 and 2 and Reference Examples 1 and 2 is a specific effect that can be exhibited only when a specific metal salt, calcium chloride and/or sodium chloride, is used in combination with an oxidative degradation agent.

The invention claimed is:

1. A biodegradable disposable body warmer comprising an inner bag and an exothermic composition,
   the exothermic composition being contained in the inner bag,
   the exothermic composition comprising an iron powder, a water-retaining agent, water, and at least one member selected from the group consisting of potassium chloride and sodium chloride,
   the inner bag being breathable,
   the inner bag comprising an oxidative degradation agent,
   the amount proportion of the potassium chloride and/or sodium chloride in the exothermic composition being about 4 to 2800 parts by mass per 100 parts by mass of the oxidative degradation agent incorporated in the inner bag,
   the proportion of water in the exothermic composition being 1 to 30 mass %, based on the total mass of the exothermic composition,
   the proportion of the oxidative degradation agent in the inner bag being 0.48 to 3.8 mass %, based on the total weight of the inner bag,
   wherein the oxidative degradation agent is a combination of a carboxylic acid having 10 to 20 carbon atoms, and the rare earth compound is at least one member selected from the group consisting of cerium, yttrium, neodymium, rare earth oxides, rare earth hydroxides, rare earth sulfates, rare earth nitrates, and rare earth chlorides.

2. The biodegradable disposable body warmer according to claim 1, wherein the inner bag is formed from a laminate comprising a breathable resin film laminated on a woven or nonwoven fabric.

3. The biodegradable disposable body warmer according to claim 2, wherein the resin forming the breathable resin film is polyolefin.

4. The biodegradable disposable body warmer according to claim 2, wherein the fiber material forming the woven or nonwoven fabric is polyolefin.

5. The biodegradable disposable body warmer according to claim 1, wherein the exothermic composition comprises potassium chloride, an iron powder, a water-retaining agent, and water.

6. The biodegradable disposable body warmer according to claim 3, wherein the fiber material forming the woven or nonwoven fabric is polyolefin.

7. The biodegradable disposable body warmer according to claim 2, wherein the exothermic composition comprises potassium chloride, an iron powder, a water-retaining agent, and water.

8. The biodegradable disposable body warmer according to claim 3, wherein the exothermic composition comprises potassium chloride, an iron powder, a water-retaining agent, and water.

9. The biodegradable disposable body warmer according to claim 4, wherein the exothermic composition comprises potassium chloride, an iron powder, a water-retaining agent, and water.

10. The biodegradable disposable body warmer according to claim 2, wherein the resin forming the breathable resin film is at least one member selected from the group consisting of polyolefin, polystyrene, polyvinyl chloride, polyvinylidene chloride, polyamide, polyester, polyvinyl alcohol, polyurethane, and polycarbonates.

11. The biodegradable disposable body warmer according to claim 2, wherein the fiber material forming the woven or nonwoven fabric is at least one member selected from the group consisting of nylon, vinylon, polyester, rayon, acetate, acrylic, polyolefin, polyvinyl chloride, cotton, hemp, and silk.

* * * * *